(12) United States Patent
Ito et al.

(10) Patent No.: US 9,846,123 B2
(45) Date of Patent: Dec. 19, 2017

(54) SURFACE-ENHANCED RAMAN SCATTERING ELEMENT

(71) Applicant: HAMAMATSU PHOTONICS K.K., Hamamatsu-shi, Shizuoka (JP)

(72) Inventors: Masashi Ito, Hamamatsu (JP); Katsumi Shibayama, Hamamatsu (JP); Yoshihiro Maruyama, Hamamatsu (JP)

(73) Assignee: HAMAMATSU PHOTONICS K.K., Hamamatsu-shi, Shizuoka (JP)

(*) Notice: Subject to any disclaimer, the term of this patent is extended or adjusted under 35 U.S.C. 154(b) by 164 days.

(21) Appl. No.: 14/420,469

(22) PCT Filed: Aug. 9, 2013

(86) PCT No.: PCT/JP2013/071710
§ 371 (c)(1),
(2) Date: Feb. 9, 2015

(87) PCT Pub. No.: WO2014/025039
PCT Pub. Date: Feb. 13, 2014

(65) Prior Publication Data
US 2015/0212002 A1    Jul. 30, 2015

(30) Foreign Application Priority Data
Aug. 10, 2012   (JP) .................................. 2012-178763

(51) Int. Cl.
*G01N 21/65* (2006.01)
*B82Y 15/00* (2011.01)
(Continued)

(52) U.S. Cl.
CPC ............ *G01N 21/658* (2013.01); *B82Y 15/00* (2013.01); *B82Y 30/00* (2013.01); *B82Y 40/00* (2013.01); *Y10S 977/781* (2013.01)

(58) Field of Classification Search
CPC .... G01N 21/65–21/658; G01N 21/553; B82Y 30/00; G02B 5/008
See application file for complete search history.

(56) References Cited

U.S. PATENT DOCUMENTS 7,428,046 B2 *   9/2008   Wang ....................... G01J 3/44
                                                          356/244
2004/0023046 A1   2/2004   Schlottig et al.
(Continued)

FOREIGN PATENT DOCUMENTS

CM   101400976   4/2009
CN   102483354   5/2002
(Continued)

OTHER PUBLICATIONS

"Q-SERS™ G1 Substrate," Opto Science, Inc. (retrieved on-line on Jul. 5, 2013).
(Continued)

*Primary Examiner* — Bumsuk Won
*Assistant Examiner* — Jeffrey Madonna
(74) *Attorney, Agent, or Firm* — Drinker Biddle & Reath LLP

(57) ABSTRACT

A surface-enhanced Raman scattering element comprises a substrate having a principal surface; a molded layer including a support part formed on the principal surface and a fine structure part formed on the support part; and a conductor layer, deposited on the fine structure part, constituting an optical functional part for generating surface-enhanced Raman scattering. The fine structure part has a plurality of pillars erected on the support part. The support part is provided with a plurality of opposing parts opposing side faces of the pillars. The opposing parts are located on the substrate side relative to leading end parts of the pillars in a projecting direction of the pillars.

17 Claims, 9 Drawing Sheets

(51) Int. Cl.
  *B82Y 40/00* (2011.01)
  *B82Y 30/00* (2011.01)

(56) References Cited

U.S. PATENT DOCUMENTS

| | | | |
|---|---|---|---|
| 2006/0146323 A1 | 7/2006 | Bratkovski et al. | |
| 2007/0015288 A1* | 1/2007 | Hulteen | G01N 21/554 436/165 |
| 2007/0153267 A1* | 7/2007 | Wang | G01N 21/658 356/301 |
| 2008/0094621 A1* | 4/2008 | Li | G01N 21/658 356/301 |
| 2008/0218761 A1 | 9/2008 | Nishikawa et al. | |
| 2011/0027901 A1 | 2/2011 | Gaster et al. | |
| 2011/0116089 A1 | 5/2011 | Schmidt et al. | |
| 2011/0166045 A1 | 7/2011 | Dhawan et al. | |
| 2013/0142987 A1* | 6/2013 | Wardle | B82B 1/00 428/98 |
| 2014/0043605 A1 | 2/2014 | Tseng et al. | |

FOREIGN PATENT DOCUMENTS

| | | |
|---|---|---|
| CN | 101281133 | 10/2008 |
| CN | 101319994 | 12/2008 |
| CN | 101408513 | 4/2009 |
| CN | 102169086 | 8/2011 |
| CN | 102282094 | 12/2011 |
| JP | H05-044867 U | 6/1993 |
| JP | H07-260646 A | 10/1995 |
| JP | 2003-026232 A | 1/2003 |
| JP | 2005-337771 A | 12/2005 |
| JP | 2007-530925 A | 11/2007 |
| JP | 2007-538264 A | 12/2007 |
| JP | 2008-519254 A | 6/2008 |
| JP | 2008-196992 A | 8/2008 |
| JP | 2008-268059 A | 11/2008 |
| JP | 2009-025316 A | 2/2009 |
| JP | 2009-047623 A | 3/2009 |
| JP | 2009-103643 A | 5/2009 |
| JP | 2009-222507 A | 10/2009 |
| JP | 2009-236830 A | 10/2009 |
| JP | 2009-544967 A | 12/2009 |
| JP | 2010-506191 A | 2/2010 |
| JP | 2011-021085 | 2/2011 |
| JP | 2011-033518 A | 2/2011 |
| JP | 2011-506916 A | 3/2011 |
| JP | 2011-075348 A | 4/2011 |
| JP | 2011-107032 A | 6/2011 |
| JP | 2011-141265 A | 7/2011 |
| JP | 2011-215021 A | 10/2011 |
| JP | 2012-233707 A | 11/2012 |
| WO | WO-2007/149120 A2 | 12/2007 |
| WO | WO-2010/050203 A1 | 5/2010 |
| WO | WO-2010/090111 A1 | 8/2010 |
| WO | WO-2011/021085 A2 | 2/2011 |
| WO | WO-2011/040504 A1 | 4/2011 |
| WO | WO-2012/024006 A2 | 2/2012 |
| WO | WO 2013/015810 | 1/2013 |
| WO | WO-2014/025033 A1 | 2/2014 |
| WO | WO-2014/025034 A1 | 2/2014 |

OTHER PUBLICATIONS

Masahiro Yanagisawa, "Detection of Trace Organic Gas Using Molecular Sensor with Plasmon Antenna," Green Technology, Vo. 22, No. 6, Jun. 10, 2012, pp. 42-47, including at least partial English-language translation.

W. Zhang et al., "Giant and uniform fluorescence enhancement over large areas using plamonic nanodots in 3D resonant cavity nanoantenna by nanoimprinting", Nanotechnolgy, vol. 23, No. 22, May 10, 2012, p. 225301, XP020224099.

S. M. Wells el al., "Efficient disc on pillar substrates for surface enhanced Raman spectroscopy", Chemical Communications—Chemcom, vol. 47, No. 13, Jan. 1, 2011, p. 3814-3816, XP055289549.

K. Nakamoto et al., "Arrays of Metallic Nanopillars in Holes for Plasmonic Devices", Retrieved from the Internet: URL: http://www.rsc.org/images/LOC/2011/PDFs/Papers/596_0021.pdf, Oct. 6, 2011, XP055289892.

M. Tomohiko et al., "New localized surface plasmon resonance sensor utilizing nanoimprinting technology", NSTI Nanotechnology Conference and Trade Show-NSTI Nanotech, vol. 1, May 11, 2006, p. 58-p. 61 XP009098538.

W. D. Li et al., "Three-dimensional cavity nanoantenna coupled plasmonic nanodots for ultrahigh and uniform surface-enhanced Raman scattering over large area", Optics Express, vol. 19, No. 5, Feb. 14, 2011, p. 3925-3936, XP002751299.

U.S. Office Action dated Oct. 14, 2016 that issued in U.S. Appl. No. 14/420,510 including Double Patenting Rejections on pp. 2-14.

English Machine Translation of JP 2011-107032, Nishikawa et al., Jun. 2, 2011 as attached to U.S. Office Action dated Oct. 14, 2016 in U.S. Appl. No. 14/420,510.

* cited by examiner

Fig.4
(a)
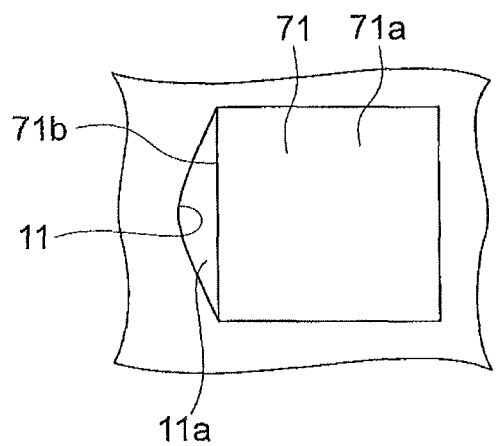
(b)
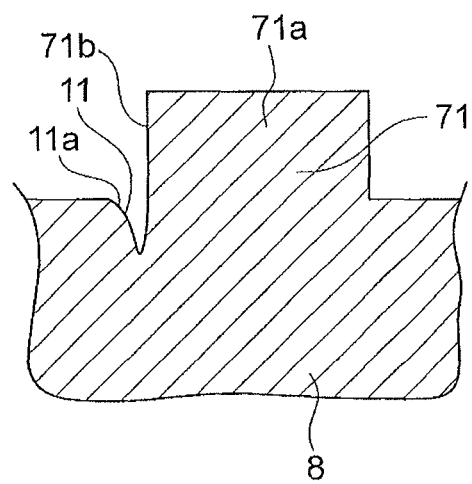

*Fig.6*
(a) 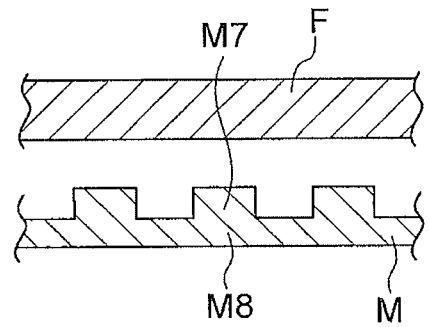
(b) 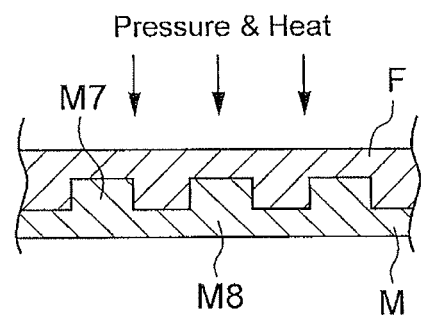
(c) 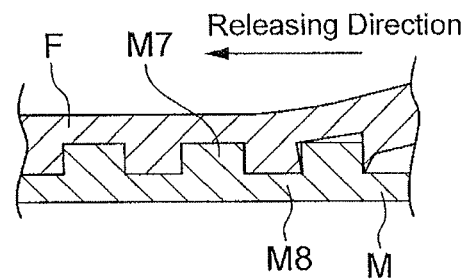
(d) 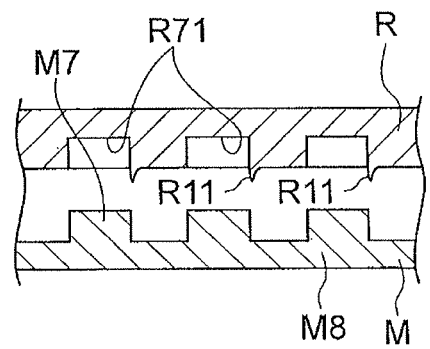

Fig.7
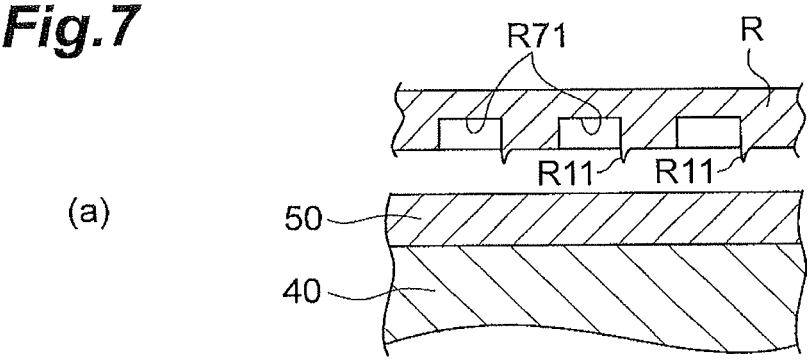
(a)
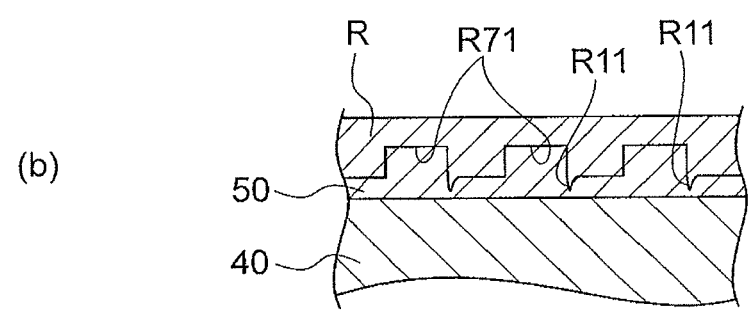
(b)
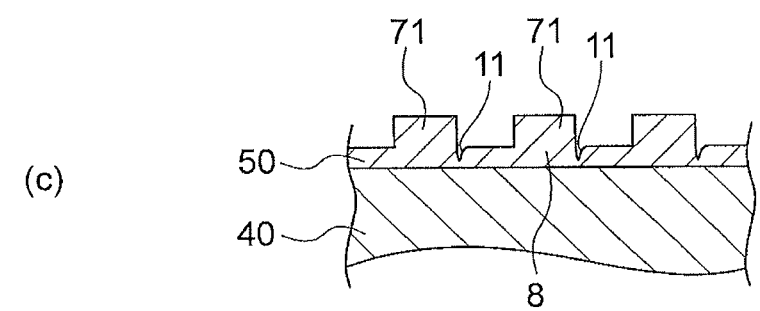
(c)
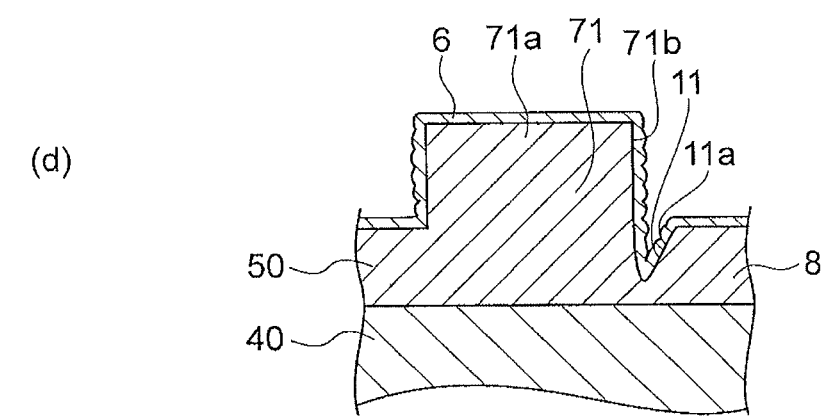
(d)

Fig.8
(a) 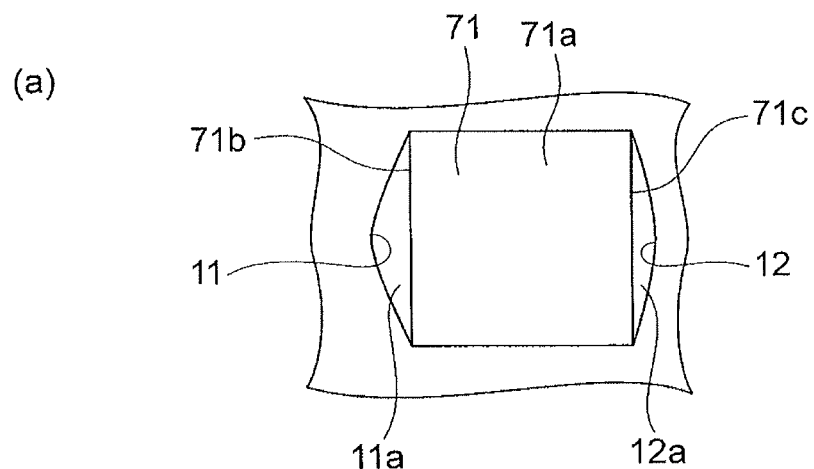
(b) 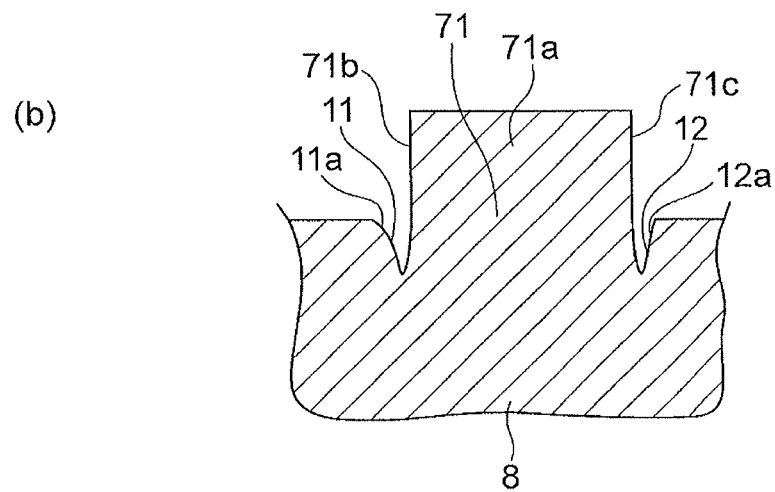

Fig.9
(a) 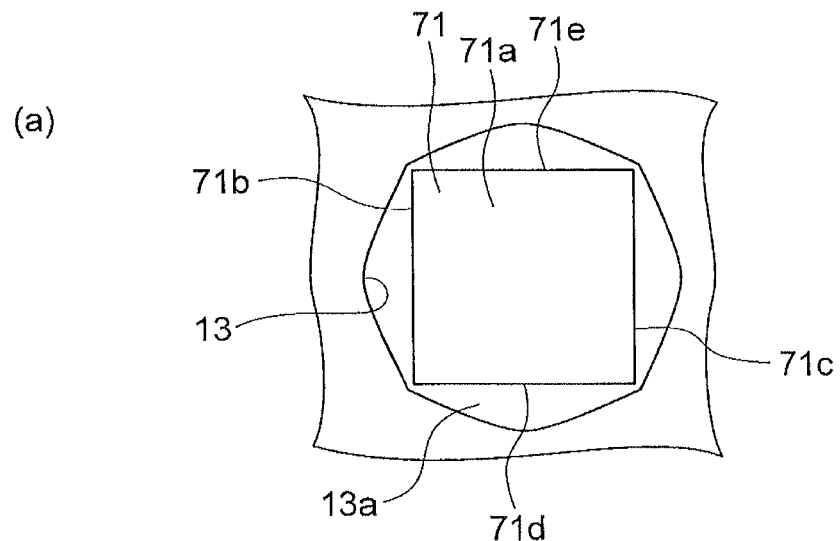
(b) 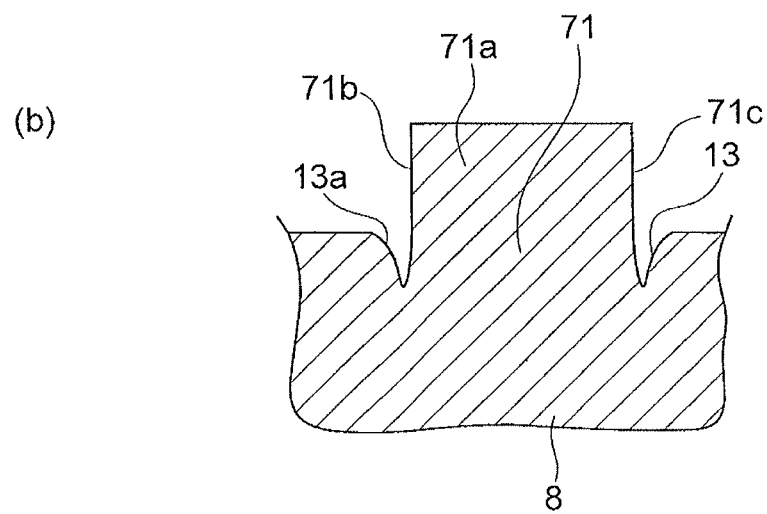

SURFACE-ENHANCED RAMAN SCATTERING ELEMENT

TECHNICAL FIELD

One aspect of the present invention relates to a surface-enhanced Raman scattering element.

BACKGROUND ART

As a conventional surface-enhanced Raman scattering element, one equipped with a minute metal structure configured to generate surface-enhanced Raman scattering (SERS) has been known (see, for example, Patent Literature 1 and Non Patent Literature 1). In such a surface-enhanced Raman scattering element, when a sample to be subjected to Raman spectroscopic analysis is brought into contact with the minute metal structure and is irradiated with excitation light in this state, surface-enhanced Raman scattering occurs, whereby Raman scattering light enhanced by about $10^8$ times, for example, is released.

Meanwhile, for example, Patent Literature 2 discloses a minute metal structure in which metal layers are formed on one surface of a substrate and upper surfaces of a plurality of minute projections formed on the one surface of the substrate (or bottom faces of a plurality of fine holes formed on the one surface of the substrate) so as to be out of contact with each other (such that the shortest distance therebetween is on the order of 5 nm to 10 µm).

CITATION LIST

Patent Literature

Patent Literature 1: Japanese Patent Application Laid-Open No. 2011-33518
Patent Literature 2: Japanese Patent Application Laid-Open No. 2009-222507

Non Patent Literature

Non Patent Literature 1: "Q-SERS™ G1 Substrate", [online], Opto Science, Inc., [retrieved on Jul. 19, 2012]. Retrieved from the Internet: <URL: http://www.optoscience.com/maker/nanova/pdf/Q-SERS_G1.pdf>.

SUMMARY OF INVENTION

Technical Problem

When a minute metal structure is formed with a so-called nanogap as mentioned above, electric fields are locally enhanced upon irradiation with excitation light, whereby the intensity of surface-enhanced Raman scattering increases.

It is therefore an object of the present invention to provide a surface-enhanced Raman scattering element which can increase the intensity of surface-enhanced Raman scattering by a favorable nanogap.

Solution to Problem

The surface-enhanced Raman scattering element in accordance with one aspect of the present invention comprises a substrate having a principal surface; a molded layer including a support part formed on the principal surface and a fine structure part formed on the support part; and a conductor layer deposited on the fine structure part and constituting an optical functional part for generating surface-enhanced Raman scattering; the fine structure part having a plurality of pillars erected on the support part, the support part being provided with a plurality of opposing parts opposing side faces of the pillars, the opposing parts being located on the substrate side relative to leading end parts of the pillars in a projecting direction of the pillars.

In this surface-enhanced Raman scattering element, the opposing parts opposing the side faces of the pillars are provided at positions on the substrate side relative to the leading end parts of the pillars. When forming the conductor layer by deposition, the amount of depositing fine conductive material particles becomes smaller on the side faces of the pillars and the opposing parts. Therefore, due to agglomerating actions of the fine conductive material particles, nanoparticles having a hemispherical outer form, for example, are formed on both of the side face of each pillar and its opposing part, while favorably producing a gap between the nanoparticles. The gaps formed on the side faces of the pillars favorably function as nanogaps where electric fields are locally enhanced. Therefore, this surface-enhanced Raman scattering element can increase the intensity of surface-enhanced Raman scattering by favorable nanogaps.

In the surface-enhanced Raman scattering element in accordance with one aspect of the present invention, the pillars may be arranged periodically along the principal surface. This configuration can stably increase the intensity of surface-enhanced Raman scattering.

In the surface-enhanced Raman scattering element in accordance with one aspect of the present invention, the support part may be formed with a plurality of depressions, the opposing parts being inner surfaces of the depressions. This configuration can form the opposing parts easily and securely.

In the surface-enhanced Raman scattering element in accordance with one aspect of the present invention, the opposing part may extend along a part of a side face of the pillar when seen in the pillar projecting direction. This configuration can increase gaps which favorably function as nanogaps.

In the surface-enhanced Raman scattering element in accordance with one aspect of the present invention, the opposing part may extend so as to surround the side face of the pillar when seen in the pillar projecting direction. This configuration can increase gaps which favorably function as nanogaps.

In the surface-enhanced Raman scattering element in accordance with one aspect of the present invention, one pillar may be provided with a plurality of opposing parts. This configuration can further increase gaps which favorably function as nanogaps.

In the surface-enhanced Raman scattering element in accordance with one aspect of the present invention, the plurality of opposing parts provided for one pillar may have respective forms different from each other. This configuration generates a predetermined orientation in the state of formation of gaps in the optical function part by forming the opposing parts similarly in terms of the relationship between pillars. Therefore, the intensity of light having a predetermined polarization direction can selectively be increased.

Advantageous Effects of Invention

The present invention can provide a surface-enhanced Raman scattering element which can increase the intensity of surface-enhanced Raman scattering by a favorable nanogap.

BRIEF DESCRIPTION OF DRAWINGS

FIG. 4(a) is a plan view of a pillar and opposing part in FIG. 3, while FIG. 4(b) is a sectional view of the pillar and opposing part in FIG. 3;

FIG. 6 is a sectional view illustrating steps of manufacturing the surface-enhanced Raman scattering unit of FIG. 1;

FIG. 7 is a sectional view illustrating steps of manufacturing the surface-enhanced Raman scattering unit of FIG. 1;

FIG. 8(a) is a plan view of a pillar and opposing part in accordance with a second embodiment, while FIG. 8(b) is a sectional view of the pillar and opposing part in accordance with the second embodiment; and FIG. 9(a) is a plan view of a pillar and opposing part in accordance with a third embodiment, while FIG. 9(b) is a sectional view of the pillar and opposing part in accordance with the third embodiment.

DESCRIPTION OF EMBODIMENTS

Figure 1:
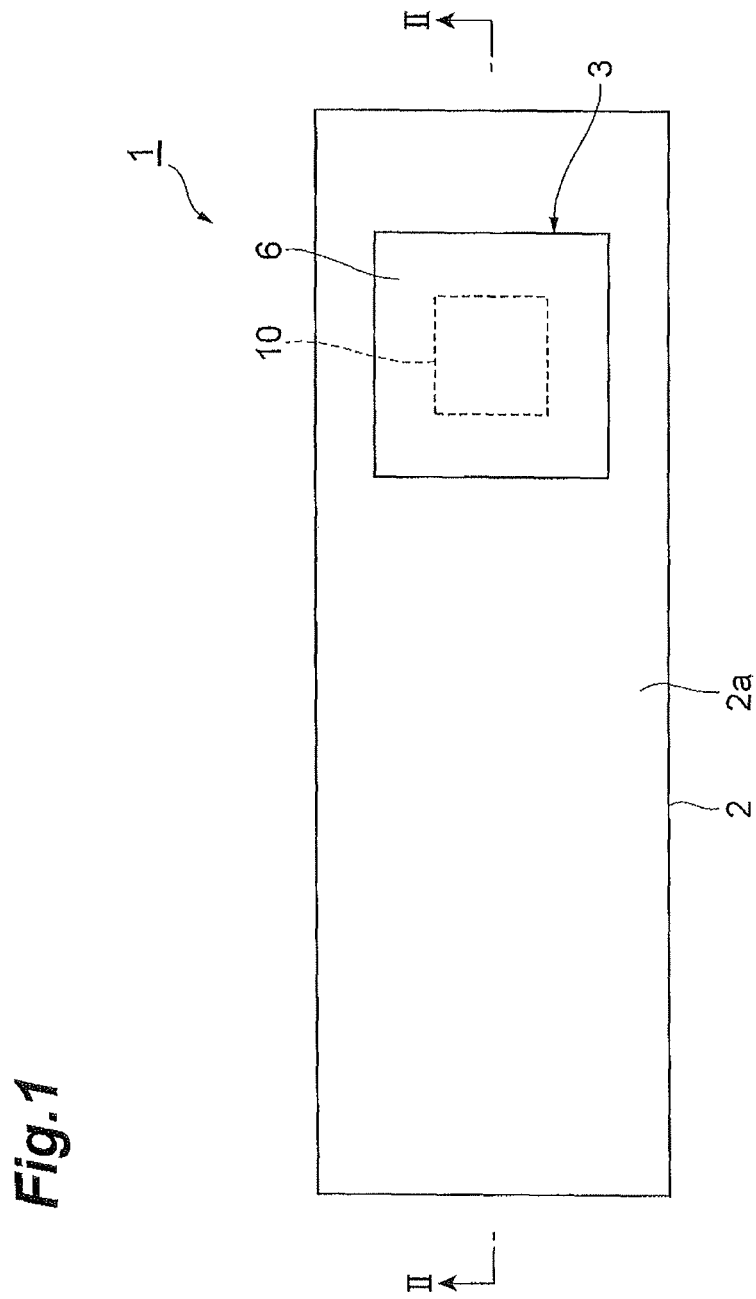
FIG. 1 is a plan view of a surface-enhanced Raman scattering unit equipped with a surface-enhanced Raman scattering element in accordance with a first embodiment of the present invention.

In the following, embodiments of the present invention will be explained in detail with reference to the drawings. In the drawings, the same or equivalent parts will be referred to with the same signs while omitting their overlapping descriptions.

First Embodiment

Figure 2:
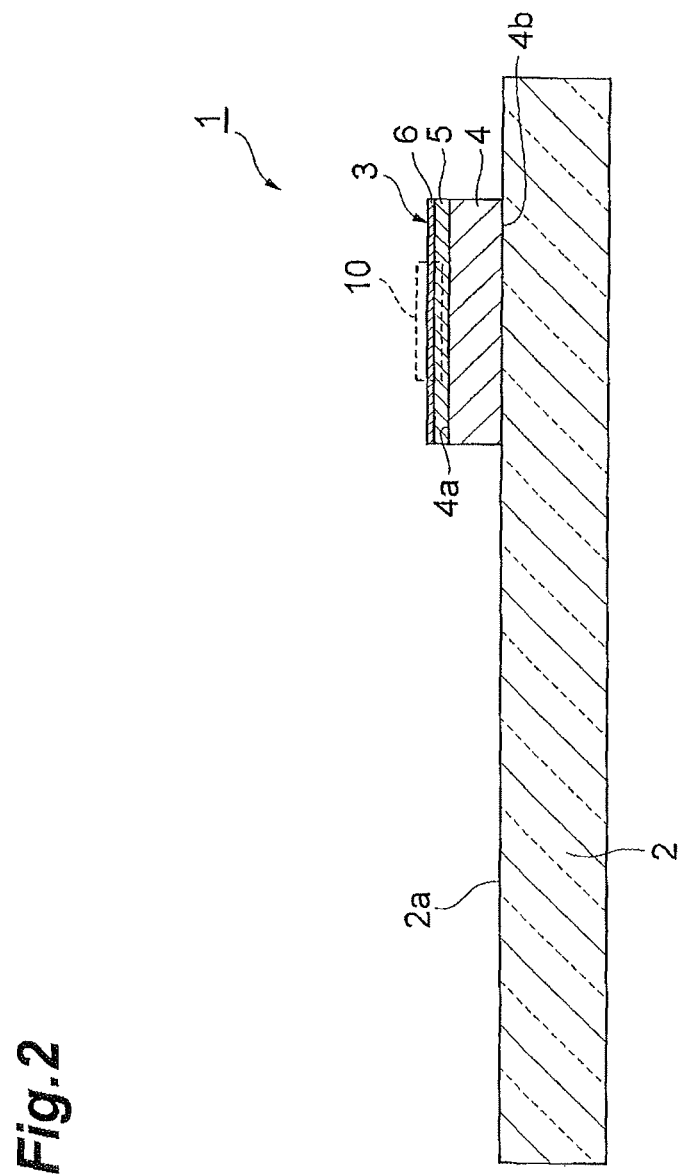
FIG. 2 is a sectional view taken along the line of FIG. 1.

As illustrated in FIGS. 1 and 2, a SERS unit (surface-enhanced Raman scattering unit) 1 in accordance with the first embodiment comprises a handling board 2 and a SERS element (surface-enhanced Raman scattering element) 3 attached onto the handling board 2. The handling board 2 is a rectangular plate-shaped glass slide, resin board, ceramic board, or the like. The SERS element 3 is arranged on a front face 2a of the handling board 2 while being biased to one end part in the longitudinal direction of the handling board 2.

The SERS element 3 comprises a substrate 4 attached onto the handling board 2, a molded layer 5 formed on the substrate 4, and a conductor layer 6 formed on the molded layer 5. The substrate 4 is formed into a rectangular plate by silicon, glass, or the like. The substrate 4 has an outer form on the order of several hundred μm×several hundred μm to several ten mm×several ten mm and a thickness on the order of 100 μm to 2 mm. A rear face 4b of the substrate 4 is secured to the front face 2a of the handling board 2 by direct bonding, bonding with a metal such as solder, eutectic bonding, fusion bonding by irradiation with laser light and the like, anodic bonding, or bonding with a resin.

Figure 3:
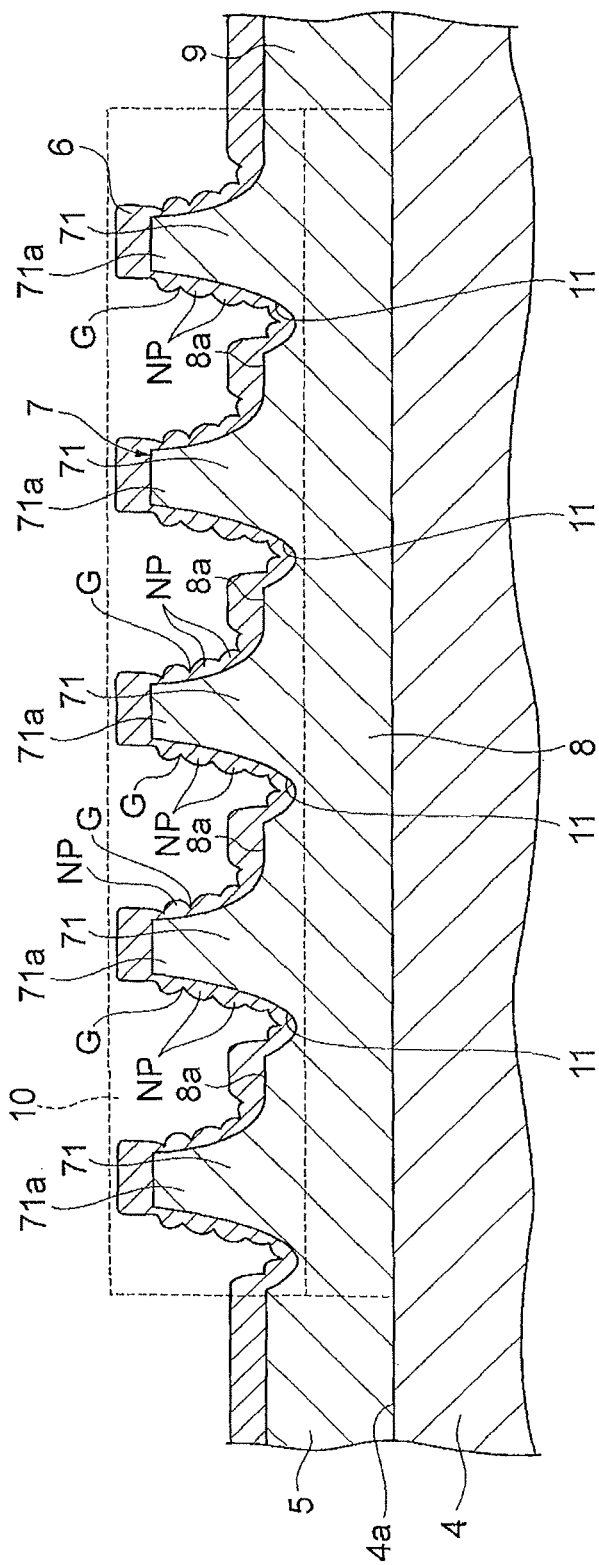
FIG. 3 is a sectional view of an optical function part in the surface-enhanced Raman scattering unit of FIG. 1.

As illustrated in FIG. 3, the molded layer 5 includes a fine structure part 7, a support part 8, and a frame part 9. The fine structure part 7 is a region having a periodic pattern. The fine structure part 7 is formed on a surface layer on the side opposite from the substrate 4 at a center part of the molded layer 5. A plurality of pillars 71, each formed into a truncated quadrangular pyramid having a diameter and height on the order of several nm to several hundred nm, are arranged on the fine structure part 7. The plurality of pillars 71 are periodically arranged at a pitch on the order of several ten nm to several hundred μm (preferably 250 nm to 800 nm) along a front face (principal surface) 4a of the substrate 4. The fine structure part 7 has a rectangular outer form on the order of several hundred μm×several hundred μm to several ten mm×several ten mm when seen in the thickness direction of the substrate 4. The support part 8 is a rectangular region supporting the fine structure part 7. The support part 8 is formed on the front face 4a of the substrate 4. The frame part 9 is a rectangular ring-shaped region surrounding the support part 8. The frame part 9 is formed on the front face 4a of the substrate 4. The support part 8 and frame part 9 have a thickness on the order of several ten nm to several ten μm. The molded layer 5 like this is integrally formed by molding a resin (examples of which include resins based on acrylics, fluorine, epoxy, silicone, and urethane, PET, polycarbonate, and inorganic/organic hybrid materials) or low-melting glass arranged on the substrate 4 by nanoimprinting, for example.

The plurality of pillars 71 are erected on the support part 8. A surface 8a of the support part 8 is exposed between the pillars 71 adjacent to each other. A plurality of depressions 11 are formed on the surface 8a of the support part 8. The depressions 11 are provided for the respective pillars 71. The depressions 11 are located on the substrate 4 side relative to leading end parts 71a of the pillars 71 in the projecting direction of the pillars 71.

As illustrated in (a) and (b) of FIG. 4, the depression 11 is provided adjacent to the pillar 71 when seen in the projecting direction of the pillars 71. Specifically, the depression 11 is defined by a side face 71b of the pillar 71 and a wall part (inner surface) 11a opposing the side face 71b. That is, the wall part 11a of the depression 11 functions as an opposing part opposing the side face 71b of the pillar 71. The wall part 11a extends along one side face 71b of the pillar 71 when seen in the projecting direction of the pillar 71. The depression 11 has a depth on the order of several nm to several hundred nm and a length (along the side face 71b) on the order of several nm to several hundred nm, for example. The largest distance between the side face 71b and wall part 11a is about several ten nm, for example.

As illustrated in FIG. 3, the conductor layer 6 is formed over the fine structure part 7 and frame part 9. In the fine structure part 7, the conductor layer 6 is formed on the outer surfaces of the pillars 71, the surface 8a of the support part 8, and the inner surfaces of the depressions 11. The conductor layer 6 has a thickness on the order of several nm to several μm. The conductor layer 6 like this is formed by vapor-depositing, spattering, or the like a conductor such as a metal (Au, Ag, Al, Cu, Pt, or the like) on the molded layer 5 molded by nanoimprinting, for example. In the SERS element 3, the conductor layer 6 formed on the fine structure part 7 and the surface 8a of the support part 8 constructs an optical function part 10 which generates surface-enhanced Raman scattering.

Figure 5:
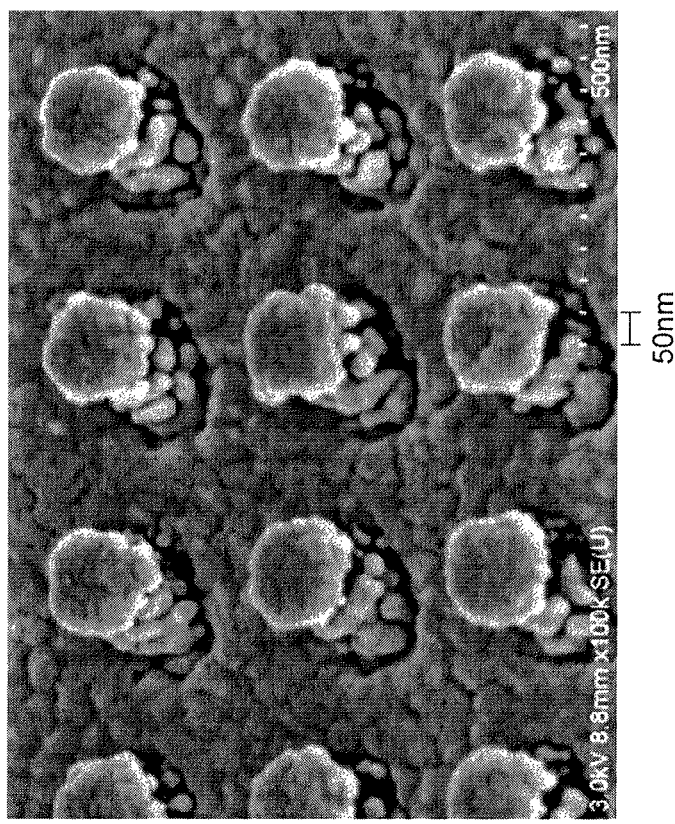
FIG. 5 is a SEM photograph of the optical function part in the surface-enhanced Raman scattering unit of FIG. 1.

FIG. 5 is a SEM photograph of the optical function part in the surface-enhanced Raman scattering unit of FIG. 1. As illustrated in FIGS. 3 and 5, the conductor layer 6 includes a plurality of nanoparticles NP formed on the side faces 71b of the pillars 71 and the wall parts 11a of the depressions 11. Each nanoparticle NP is formed into a substantially hemispherical shape. A gap G is formed between the nanoparticles NP adjacent to each other.

The SERS unit 1 constructed as in the foregoing is used as follows. First, a ring-shaped spacer made of silicone, for example, is arranged on the front face 2a of the handling board 2 so as to surround the SERS element 3. Subsequently, a sample of a solution (or a dispersion of a powder sample in a solution such as water or ethanol) is dropped to the inside of the spacer with a pipette or the like. This arranges the sample on the optical function part 10. Then, for reducing the lens effect, a glass cover is mounted on the spacer and brought into close contact with the solution sample.

Next, the SERS unit 1 is set in a Raman spectroscopic analyzer, and the sample arranged on the optical function part 10 is irradiated with excitation light through the glass cover. This generates surface-enhanced Raman scattering at the interface between the optical function part 10 and sample, whereby surface-enhanced Raman scattering light derived from the sample is enhanced by about $10^8$ times, for example, and released. Hence, the Raman spectroscopic analyzer enables Raman spectroscopy with high sensitivity and high accuracy.

Not only the above-mentioned method, but the following methods may also be used for arranging the sample on the optical function part 10. For example, while holding the handling board 2, the SERS element 3 may be dipped in and lifted from the solution sample (or a dispersion of a powder sample in a solution such as water or ethanol), and then the sample may be blown to dry. A minute amount of the solution sample (or a dispersion of a powder sample in a solution such as water or ethanol) may be dropped onto the optical function part 10 and left to dry. A powder sample may be dispersed as it is on the optical function part 10.

An example of methods for manufacturing the SERS unit 1 in accordance with the first embodiment will now be explained. First, as illustrated in (a) of FIG. 6, a master mold M and a film base F are prepared. The master mold M includes a fine structure part M7 corresponding to the fine structure part 7 and a support part M8 for supporting the fine structure part M7. A plurality of fine structure parts M7 are arranged in a matrix on the support part M8. Subsequently, as illustrated in (b) of FIG. 6, the film base F is pressed against the master mold M and pressurized and heated in this state. This transfers a pattern of the plurality of fine structure parts M7 to the film base F.

Next, as illustrated in (c) of FIG. 6, the film base F is released from the master mold M. This yields a replica mold (replica film) R having the pattern of the plurality of fine structure parts M7 transferred thereto as illustrated in (d) of FIG. 6. Various conditions are controlled at the time of releasing. For example, as illustrated in (c) of FIG. 6, the releasing direction of the film base F with respect to the master mold M can be controlled. At least one of the tensile load, releasing speed, and the like can also be controlled, for example.

As illustrated in (d) of FIG. 6, the replica mold R is formed with pillar-forming depressions R71. Controlling the releasing direction as mentioned above forms depression-forming parts R11 in parts which have been in contact with the support part M8 of the master mold M and are adjacent to the pillar-forming depressions R71. More specifically, the depression-forming parts R11 are formed at positions released earlier than the pillar-forming depressions R71.

Next, as illustrated in (a) of FIG. 7, a silicone wafer 40 to become the substrate 4 is prepared. A UV-curable resin is applied to a front face 40a of the silicon wafer 40, so as to form a nanoimprinting layer 50 to become the molded layer 5 on the silicone wafer 40. Subsequently, as illustrated in (b) of FIG. 7, the replica mold R is pressed against the nanoimprinting layer 50, and the nanoimprinting layer 50 is irradiated with UV in this state, so as to be cured. This transfers the pattern of the replica mold R to the nanoimprinting layer 50. Then, as illustrated in (c) of FIG. 7, the replica mold R is released from the nanoimprinting layer 50. This yields the silicone wafer 40 formed with a plurality of fine structure parts 7.

Next, as illustrated in (d) of FIG. 7, a film of a metal such as Au or Ag is formed on the molded layer 5 by vapor deposition such as resistance heating vapor deposition or electron beam vapor deposition, sputtering, or the like, so as to form the conductor layer 6. At this time, the amount of depositing fine metal particles becomes smaller on the side face 71b of the pillar 71 and the wall part 11a of the depression 11. Therefore, due to agglomerating actions of the fine metal particles, nanoparticles NP are formed on both of the side face 71b and wall part 11a. The amount of depositing fine metal particles also becomes smaller on the other side faces of the pillar 71, thereby forming the nanoparticles NP.

When depositing the conductor layer, the fine metal particles adhere to the molded layer 5 while having energy. At this time, the energy is conserved, whereby the fine metal particles attached to the molded layer move slightly on the molded layer 5. The movement of the fine metal particles attached to the molded layer 5 between the side face 71b and wall part 11a is considered to be different from that in flat places. This also seems to form the nanoparticles NP.

When depositing the conductor layer, the fine metal particles are deemed to bounce off corners of the depression 11 (parts where the wall part 11a and the surface of the support part 8 intersect) toward the side face 71b. This also seems to form the nanoparticles NP on the side face 71b.

Next, the silicone wafer 40 is cut for each fine structure part 7 (i.e., for each optical function part 10), whereby a plurality of SERS elements 3 are obtained. Subsequently, the SERS element 3 is attached onto the handling board 2, so as to yield the SERS unit 1.

In the SERS element 3, as in the foregoing, the wall parts 11a opposing the side faces 71b of the pillars 71 are provided at positions on the substrate 4 side relative to the leading end parts 71a of the pillars 71. When forming the conductor layer 6 by deposition, the amount of depositing fine conductive material particles becomes smaller on the side faces 71b of the pillars 71 and the wall parts 11a. Therefore, due to agglomerating actions of the fine conductive material particles, the nanoparticles NP having a hemispherical outer form, for example, are formed on both of the side face 71b of the pillar 71 and the wall part 11a, while favorably producing the gap G between the nanoparticles NP, NP. The gaps G formed on the side faces 71b of the pillars 71 favorably function as nanogaps where electric fields are locally enhanced. Therefore, this SERS element 3 can increase the intensity of surface-enhanced Raman scattering by favorable nanogaps.

In the above-mentioned SERS element 3, the pillars 71 are arranged periodically along the principal surface 4a. This can stably increase the intensity of surface-enhanced Raman scattering.

In the above-mentioned SERS element 3, the support part 8 is formed with a plurality of depressions 11, while the wall parts 11a are inner surfaces of the depressions 11. The inventors conducted diligent studies and, as a result, have found that the depression-forming parts R11 in the form of projections can easily be formed near the pillar-forming depressions R71 for molding the pillars in the replica mold R by controlling conditions for releasing the film base F from the master mold M when producing the replica mold R as mentioned above. When the opposing parts are the wall parts 11a serving as the inner surfaces of the depressions 11 as in the above-mentioned SERS element 3, the depression-forming parts R11 can easily produce the wall parts 11a at the time of forming the molded layer 5 by nanoimprinting. Therefore, the opposing parts can be formed easily and securely.

In the above-mentioned SERS element 3, the wall part 11a extends along the side face 71b, which is a part of the side faces of the pillar 71, when seen in the projecting direction of the pillar 71. This can increase the gaps G favorably functioning as nanogaps.

Second Embodiment

FIG. 8 is a set of plan and sectional views of a pillar and opposing part in accordance with the second embodiment of the present invention. The SERS element 3 in accordance with the second embodiment differs from the SERS element 3 in accordance with the above-mentioned first embodiment mainly in that a plurality of depressions 11, 12 are provided for one pillar 71.

Specifically, the support part 8 is formed with the depression 12 in addition to the depression 11. The depression 12 is provided on the opposite side of the pillar 71 from the depression 11. The depression 12 is disposed adjacent to the pillar 71 when seen in the projecting direction of the pillar 71. More specifically, the depression 12 is defined by a side face 71c of the pillar 71 and a wall part (inner surface) 12a opposing the side face 71c. That is, the wall part 12a of the depression 12 functions as an opposing part opposing the side face 71c of the pillar 71. The depression 12 extends along one side face 71c of the pillar 71 when seen in the projecting direction of the pillar 71.

The plurality of depressions 11, 12 provided for one pillar 71 have respective forms different from each other, while the wall parts 11a, 12a have respective forms different from each other. More specifically, the depression 12 is smaller than the depression 11, while the wall part 12a is smaller than the wall part 11a.

The SERS unit 1 constructed as in the foregoing can be manufactured as follows, for example. That is, adjusting at least one of the temperature, tensile load, and the like at the time of releasing the film base F from the master mold M when producing the replica mold R by thermal nanoimprinting in the above-mentioned manufacturing method can form two depression-forming parts corresponding to the respective depressions 11, 12 adjacent to the pillar-forming depression R71. Performing the remaining steps as mentioned above by using thus obtained replica mold can manufacture a SERS unit having the depressions 11, 12.

As in the foregoing, the SERS element 3 in accordance with the second embodiment is provided with the wall part 11a opposing the side face 71b of the pillar 71 and the wall part 12a opposing the side face 71c of the pillar 71. When forming the conductor layer 6 by deposition, the amount of depositing fine conductive material particles becomes smaller on the side faces 71b, 71c of the pillar 71 and the wall parts 11a, 12a. Therefore, due to agglomerating actions of the fine conductive material particles, the nanoparticles NP having a hemispherical outer form, for example, are formed on both of the side faces 71b, 71c of the pillar 71 and the wall parts 11a, 12a, while favorably producing the gap G between the nanoparticles NP, NP. Hence, the intensity of surface-enhanced Raman scattering can be increased by favorable nanogaps.

In the above-mentioned SERS element 3, the pillars 71 are arranged periodically along the principal surface 4a. This can stably increase the intensity of surface-enhanced Raman scattering.

In the above-mentioned SERS element 3, the support part 8 is formed with a plurality of depressions 11 and a plurality of depressions 12, the wall parts 11a are inner surfaces of the depressions 11, and the wall parts 12a are inner surfaces of the depressions 12. Therefore, as mentioned above, controlling conditions for releasing the film base F from the master mold M when producing the replica mold R by thermal nanoimprinting can form the wall parts 11a, 12a easily and reliably.

In the above-mentioned SERS element 3, the wall part 11a extends along the side face 71b, which is a part of the side faces of the pillar 71, when seen in the projecting direction of the pillar 71, while the wall part 12a extends along the side face 71c, which is a part of the side faces of the pillar 71, when seen in the projecting direction of the pillar 71. This can increase the gaps G favorably functioning as nanogaps.

In the above-mentioned SERS element 3, a plurality of wall parts 11a, 12a are provided for one pillar 71. This can increase the gaps G favorably functioning as nanogaps.

In the above-mentioned SERS element 3, a plurality of wall parts 11a, 12a provided for one pillar 71 have respective forms different from each other. This generates a predetermined orientation in the state of formation of the gaps G in the optical function part 10 by forming the wall parts 11a, 12a similarly in terms of the relationship between pillars 71. Therefore, the intensity of light having a predetermined polarization direction can selectively be increased.

Third Embodiment

FIG. 9 is a set of plan and sectional views of a pillar and opposing part in accordance with the third embodiment of the present invention. The SERS element 3 in accordance with the third embodiment differs from the SERS element 3 in accordance with the above-mentioned first embodiment mainly in that a depression 13 is formed so as to surround side faces of the pillar 71.

Specifically, the support part 8 is formed with the depression 13. The depression 13 is provided adjacent to the pillar 71 when seen in the projecting direction of the pillar 71. More specifically, the depression 13 is defined by side faces 71b, 71c, 71d, 71e of the pillar 71 and a wall part (inner surface) 13a opposing the side faces 71b, 71c, 71d, 71e. That is, the wall part 13a of the depression 13 functions as an opposing part opposing the side faces 71b, 71c, 71d, 71e of the pillar 71. The wall part 13a extends so as to surround the side faces 71b, 71c, 71d, 71e of the pillar 71 when seen in the projecting direction of the pillar 71.

The SERS unit 1 constructed as in the foregoing can be manufactured as follows, for example. That is, pulling up the film base F in its thickness direction at the time of releasing the film base F from the master mold M when producing the replica mold by thermal nanoimprinting in the above-mentioned manufacturing method can form a depression-forming part corresponding to the depression 13 so as to make it surround the pillar-forming depression R71. Performing the remaining steps as mentioned above by using thus obtained replica mold can manufacture a SERS unit having the wall part 13a.

As in the foregoing, the SERS element 3 in accordance with the third embodiment is provided with the wall part 13a opposing the side faces 71b, 71c, 71d, 71e of the pillar 71. When forming the conductor layer 6 by deposition, the amount of depositing fine conductive material particles becomes smaller on the side faces 71b, 71c, 71d, 71e of the pillar 71 and the wall part 13a. Therefore, due to agglomerating actions of the fine conductive material particles, the nanoparticles NP having a hemispherical outer form, for example, are formed on both of the side faces 71b, 71c, 71d, 71e of the pillar 71 and the wall part 13a, while favorably producing the gap G between the nanoparticles NP, NP. Hence, the intensity of surface-enhanced Raman scattering can be increased by favorable nanogaps.

In the above-mentioned SERS element 3, the pillars 71 are arranged periodically along the principal surface 4a. This can stably increase the intensity of surface-enhanced Raman scattering.

In the above-mentioned SERS element 3, the support part 8 is formed with a plurality of depressions 13, while the wall parts 13a are inner surfaces of the depressions 13. Therefore, as mentioned above, controlling conditions for releasing the film base F from the master mold M when producing the replica mold R by thermal nanoimprinting can form the wall parts 13a easily and reliably.

In the above-mentioned SERS element 3, the wall part 13a extends so as to surround the side faces 71b, 71c, 71d, 71e of the pillar 71 when seen in the projecting direction of the pillar 71. This can increase the gaps G favorably functioning as nanogaps.

While the first to third embodiments of the present invention are explained in the foregoing, the present invention is not limited to the above-mentioned embodiments. For example, the cross-sectional form of the pillar 71 is not limited to quadrangles, but may be any of polygons such as triangles, circles, ellipses, and the like. Thus, without being restricted to those mentioned above, various materials and forms can be employed for the above-mentioned constituents of the SERS element 3.

The forming of the depressions 11, 12, 13 is not limited to that based on the parameter adjustment at the time of releasing the master mold M and film base F as mentioned above. For example, the master mold M is provided with depressions corresponding to the depressions 11, 12, 13, so as to produce depression-forming parts in the replica mold R. The depressions 11, 12, 13 may be formed by pressing the replica mold R against the nanoimprinting layer 50. In this case, the replica mold R may be formed from silica, silicon, nickel, or the like without being restricted to the film base F. The mold may be provided with projections corresponding to the depressions 11, 12, 13 and pressed against the nanoimprinting layer 50, so as to form the depressions 11, 12, 13 without the replica mold R.

The conductor layer 6 is not limited to the one directly formed on the fine structure part 7, but may be formed indirectly on the fine structure part 7 with a layer such as a buffer metal (Ti, Cr, or the like) for improving the adhesion of a metal to the fine structure part 7, for example, interposed therebetween.

While the wall parts 11a, 12a, 13a, which are inner surfaces of the depressions 11, 12, 13, function as opposing parts, projections projecting from the support part 8 may be provided so as to oppose side faces of the pillars 71 and employed as opposing parts. In this case, the projections can function as with the above-mentioned wall parts 11a, 12a, 13a when placed adjacent to the pillars 71 so as to reduce the number of fine metal particles passing between the side face of each pillar 71 and the side face of each projection at the time of depositing the conductor layer and provided with a height lower than that of the pillar 71 (i.e., the projections serving as the opposing parts are located on the substrate 4 side relative to the leading end parts of the pillars in the projecting direction of the pillars). In this case, the distance between the pillar and projection is made smaller than that between the periodically arranged pillars 71.

INDUSTRIAL APPLICABILITY

The present invention can provide a surface-enhanced Raman scattering element which can increase the intensity of surface-enhanced Raman scattering by a favorable nanogap.

REFERENCE SIGNS LIST

3: SERS element (surface-enhanced Raman scattering element); 4: substrate; 4a: front face (principal surface); 5: molded layer; 6: conductor layer; 7: support part; 8: fine structure part; 10: optical function part; 11, 12, 13: depression; 11a, 12a, 13a: wall part (opposing part); 71: pillar; 71a: leading end part; 71b, 71c, 71d, 71e: side face.

The invention claimed is:

1. A surface-enhanced Raman scattering element comprising:
    a substrate having a principal surface;
    a molded layer including a support part formed on the principal surface and a fine structure part formed on the support part; and
    a conductor layer deposited on the fine structure part and constituting an optical functional part for generating surface-enhanced Raman scattering;
    wherein the fine structure part has a plurality of pillars erected on the support part;
    wherein the support part is provided with a plurality of opposing parts opposing side faces of the pillars;
    wherein the opposing parts are located on a substrate side relative to leading end parts of the pillars in a projecting direction of the pillars, at least some of the opposing parts being located on or near the substrate surface; and
    wherein the support part, the pillars, and the opposing parts are integrally formed from same materials.

2. A surface-enhanced Raman scattering element according to claim 1, wherein the pillars are arranged periodically along the principal surface.

3. A surface-enhanced Raman scattering element according to claim 1, wherein the support part is formed with a plurality of depressions; and wherein the opposing parts are inner surfaces of the depressions.

4. A surface-enhanced Raman scattering element according to claim 1, wherein the opposing part extends along a part of a side face of the pillar when seen in the pillar projecting direction.

5. A surface-enhanced Raman scattering element according to claim 1, wherein the opposing part extends so as to surround the side face of the pillar when seen in the pillar projecting direction.

6. A surface-enhanced Raman scattering element according to claim 1, wherein one of the pillars is provided with a plurality of the opposing parts.

7. A surface-enhanced Raman scattering element according to claim 6, wherein the plurality of opposing parts provided for the one pillar have respective forms different from each other.

8. A surface-enhanced Raman scattering element comprising:
- a support part;
- a fine structure part formed on the support part; and
- a conductor layer deposited on the fine structure part and constituting an optical functional part for generating surface-enhanced Raman scattering;
- wherein the fine structure part has a plurality of pillars erected on the support part;
- wherein the support part is formed with a plurality of depressions;
- wherein the depressions are located on a support part side relative to leading end parts of the pillars in a projecting direction of the pillars;
- wherein the depressions are formed so as to surround a side face of the pillar when seen in the pillar projecting direction; and
- wherein the support part, the pillars, and the depressions are integrally formed from same materials.

9. A surface-enhanced Raman scattering element according to claim 8, wherein the pillars are arranged periodically when seen in the pillar projecting direction.

10. A surface-enhanced Raman scattering element according to claim 9, wherein the pillars are arranged periodically at a pitch of 250 nm to 800 nm.

11. A surface-enhanced Raman scattering element according to claim 8, wherein the cross-sectional form of the pillar is a circle.

12. A surface-enhanced Raman scattering element according to claim 8, wherein the side face of the pillar is formed with nanoparticles.

13. A surface-enhanced Raman scattering element comprising:
- a support part;
- a fine structure part formed on the support part; and
- a conductor layer deposited on the fine structure part and constituting an optical functional part for generating surface-enhanced Raman scattering;
- wherein the fine structure part has a plurality of pillars erected on the support part;
- wherein the support part is formed with a plurality of projections;
- wherein the projections are located on a support part side relative to leading end parts of the pillars in a projecting direction of the pillars;
- wherein the projections are formed so as to surround a side face of the pillar when seen in the pillar projecting direction; and
- wherein the support part, the pillars, and the projections are integrally formed from same materials.

14. A surface-enhanced Raman scattering element according to claim 13, wherein the pillars are arranged periodically when seen in the pillar projecting direction.

15. A surface-enhanced Raman scattering element according to claim 14, wherein the pillars are arranged periodically at a pitch of 250 nm to 800 nm.

16. A surface-enhanced Raman scattering element according to claim 13, wherein the cross-sectional form of the pillar is a circle.

17. A surface-enhanced Raman scattering element according to claim 13, wherein the side face of the pillar is formed with nanoparticles.

* * * * *